(12) United States Patent
Baurmeister et al.

(10) Patent No.: US 6,395,935 B1
(45) Date of Patent: May 28, 2002

(54) USE OF PHOSPHORIC ACID AS A HOMOGENEOUS CATALYST DURING THE PREPARATION OF KETENE

(75) Inventors: Jochen Baurmeister, Eckernförde; Thomas Schäfer, Heppenheim, both of (DE)

(73) Assignee: Axiva GmbH (DE)

( * ) Notice: Subject to any disclaimer, the term of this patent is extended or adjusted under 35 U.S.C. 154(b) by 0 days.

(21) Appl. No.: 09/485,257

(22) PCT Filed: Jul. 24, 1998

(86) PCT No.: PCT/EP98/04654

§ 371 (c)(1),
(2), (4) Date: Apr. 27, 2000

(87) PCT Pub. No.: WO99/07662

PCT Pub. Date: Feb. 18, 1999

(30) Foreign Application Priority Data

Aug. 7, 1997 (DE) .......................................... 197 34 275

(51) Int. Cl.[7] .............................................. C07C 45/87

(52) U.S. Cl. ....................................................... 568/302
(58) Field of Search ......................................... 568/302

(56) References Cited

U.S. PATENT DOCUMENTS

| 2,278,537 A | 4/1942 | Dreyfus et al. ............. 260/547 |
| 2,856,426 A | 10/1958 | Estabrook ................... 260/547 |
| 3,378,583 A | 4/1968 | van Bogaert ............... 260/547 |
| 3,836,583 A | 9/1974 | Matthias et al. ......... 260/585.5 |

FOREIGN PATENT DOCUMENTS

| DE | 2059292 | 6/1972 |
| GB | 478303 | 1/1938 |

*Primary Examiner*—Sreeni Padmanabhan
*Assistant Examiner*—J. Parsa
(74) *Attorney, Agent, or Firm*—Connolly Bove Lodge & Hutz LLP

(57) ABSTRACT

The invention relates to a process for the catalytic pyrolysis of acetic acid for preparing ketene and/or secondary products, which comprises spraying, as catalyst, phosphoric acid in the form of a liquid jet into the acetic acid vapor.

8 Claims, 1 Drawing Sheet

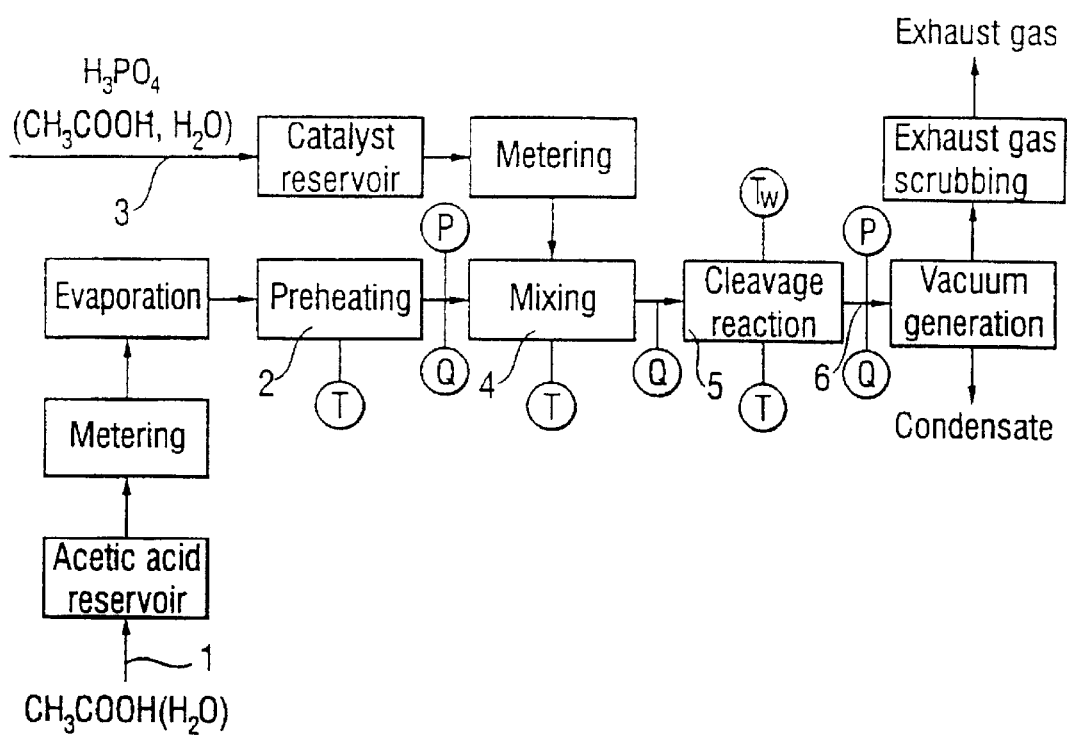

USE OF PHOSPHORIC ACID AS A HOMOGENEOUS CATALYST DURING THE PREPARATION OF KETENE

This application is a 371 of PCT/EP98/04654 filed on Jul. 24, 1998.

The invention relates to a process for the homogeneously catalyzed acetic acid pyrolysis for the preparation of ketene and/or secondary products.

The homogeneously catalyzed pyrolysis of acetic acid is carried out on an industrial scale for the production of acetic anhydride, diketene and ketene. Ketene is further processed directly to form secondary products, e.g. sorbic acid and dimethylacrylolactone. The reaction proceeds at elevated temperatures in the range from 400 to 800° C. and at reduced pressure. In addition to the principal products water and ketene, under said reaction conditions, a series of by-products are formed, e.g. carbon monoxide, carbon dioxide, ethene, ethyne, methane, propadiene and hydrogen. After the reaction, in the further course of the process, unreacted acetic acid and water are condensed out and the process gases are scrubbed with acetic anhydride. The following process steps depend on the target product.

Hitherto, only phosphoric acid derivatives having a defined vapor pressure, e.g. liquid triethyl phosphate having a boiling point of 215° C., have been used on an industrial scale for the catalysis of the process. These are comparatively expensive, however. DE 687 065 does disclose using phosphoric acid as a catalyst, but only under the conditions of heterogeneous catalysis and on a laboratory scale.

The heterogeneous processes proposed in the older patent literature have not been able to establish themselves in industrial practice, since the ketene yields are much lower in comparison with homogeneous catalysis, e.g. using triethyl phosphate, and catalyst beds of phosphoric acid derivatives and phosphates are rapidly deactivated under the reaction conditions by the coke coating and led to a blockage of the reactor.

The object underlying the invention, therefore, was to improve the process mentioned at the outset by identifying cheaper homogeneous catalysts having the same or better catalytic action as triethyl phosphate.

It has now surprisingly been found that the same ketene selectivity and the same acetic acid conversion rate in comparison with triethyl phosphate can be obtained if, as catalyst, phosphoric acid is sprayed in liquid form into the acetic acid vapor.

This contradicts previous studies and literature data, according to which the catalytic activity of triethyl phosphate is said to be significantly better and is all the more surprising since phosphoric acid is considered to be of low volatility, has no defined boiling point and, on evaporation, higher-molecular weight condensation products are formed with elimination of water. The condensation products of phosphoric acid (e.g. metaphosphoric acid and phosphorus oxides) formed at high temperature are expected to block the plants.

The invention therefore relates to a process for the homogeneously catalyzed acetic acid pyrolysis for preparing ketene and/or secondary products, which comprises spraying, as catalyst, phosphoric acid in the form of a liquid jet into the acetic acid vapor.

The term phosphoric acid in the context of the invention includes all oxygen acids of phosphorus and solutions of their anhydrides, in each case individually or in a mixture. Preference is given to orthophosphoric acid, solutions of metaphosphoric acids, oligomers of phosphoric acid and phosphorus pentoxide. The molar content of phosphoric acid is preferably 100 to 10,000 ppm, calculated as the molar content of elemental phosphorus (P), based on the amount of pure acetic acid ($CH_3COOH$) used in total.

Particular embodiments are given by the subclaims.

The phosphoric acid is preferably sprayed into the acetic acid vapor in the liquid state as commercial phosphoric acid (75, 80 or 85%) or diluted at elevated temperature. It can be added diluted with inorganic or organic solvents, preferably with water, methanol, ethanol, acetic anhydride or acetone.

In a preferred embodiment, the phosphoric acid is diluted with water or acetic acid in a ratio up to at most 1:100 and is sprayed at temperatures above 400° C. as a continuous liquid jet at high impulse in the acetic acid main stream. That means that the velocity of the liquid jet is at least 10 times higher than that of the acetic acid main stream. This avoids contact of the liquid jet with the walls. As a result of the high temperature and good mixing with the preheated acetic acid, the phosphoric acid is successfully evaporated as rapidly as possible and virtually completely. Under these conditions, the same catalytic activity of phosphoric acid and triethyl phosphate was observed. Solid deposits in the area of the catalyst admixture and in the reactor did not occur during this.

In further preferred embodiments, the catalyst is added with addition of gas, preferably with nitrogen or ammonia, and/or it is added via nozzles, preferably via ultrasonic nozzles or two-component nozzles.

BRIEF DESCRIPTION OF DRAWING

An exemplary embodiment of the invention is described in more detail below with reference to the simplified flow chart depicted in the FIGURE. No restriction of the invention in any way is intended thereby.

According to the figure, acetic acid 1 is heated (600° C.) in a preheater 2, then admixed with a catalyst 3, intensively mixed in a heated mixer 4 with the catalyst 3 which is added in liquid form, and reacted in a heated reactor 5. The resulting reaction mixture 6 is withdrawn from the reactor 5. Samples are withdrawn from the process gas streams by means of pumps upstream of the mixer 4, upstream of the reactor 5 and downstream of the reactor 5 and fed to a mass spectrometer for analysis. Control is accomplished by a process control system which is not shown.

The following experiments likewise serve for more detailed explanation of the invention, without restricting this thereby.

A phosphoric acid solution in water and acetic acid was admixed in such an experimental apparatus at 580° C. and a pressure of 300 mbar to a preheated acetic acid stream as a continuous liquid jet. Apparently the temperature is high enough so that the phosphoric acid (PA) is converted completely to the gas phase with formation of the catalytically active species. The reaction in a tubular reactor at 300 mbar, mean residence times of 0.5 to 5 s and exit temperatures of 650 to 750° C. led in each case to the same product spectrum which is obtained from comparative experiments using triethyl phosphate (TEP) as catalyst.

Experimental conditions and results of some selected experiments are summarized in the table below.

TABLE

Comparison of the catalytic activity of triethyl phosphate and phosphoric acid

| | Experimental conditions | | | Catalysts and solvents | | | | Results | |
|---|---|---|---|---|---|---|---|---|---|
| Experiment | p in mbar | T in °C. | HOAc total in g/h | Catalyst | Amount of catalyst in g/h | HOAc (catalyst) in g/h | $H_2O$ (catalyst) in g/h | Conversion rate in % | Selectivity in % |
| TEP_1 | 300 | 650 | 1286 | TEP | 3.90 | 8.8 | 13.2 | 26.65 | 98.09 |
| TEP_2 | 300 | 670 | 1286 | TEP | 3.90 | 8.8 | 13.2 | 34.53 | 96.38 |
| TEP_3 | 300 | 690 | 1286 | TEP | 3.90 | 8.8 | 13.2 | 48.13 | 94.18 |
| TEP_4 | 300 | 710 | 1286 | TEP | 3.90 | 8.8 | 13.2 | 62.97 | 95.44 |
| TEP_5 | 300 | 730 | 1286 | TEP | 3.90 | 8.8 | 13.2 | 74.55 | 94.34 |
| TEP_6 | 300 | 750 | 1286 | TEP | 3.90 | 8.8 | 13.2 | 85.59 | 92.98 |
| PA_1 | 300 | 650 | 1286 | $H_3PO_4$ | 2.10 | 8.8 | 13.2 | 25.46 | 98.82 |
| PA_2 | 300 | 670 | 1286 | $H_3PO_4$ | 2.10 | 8.8 | 13.2 | 33.32 | 96.75 |
| PA_3 | 300 | 690 | 1286 | $H_3PO_4$ | 2.10 | 8.8 | 13.2 | 47.78 | 95.06 |
| PA_4 | 300 | 710 | 1286 | $H_3PO_4$ | 2.10 | 8.8 | 13.2 | 64.51 | 95.00 |
| PA_5 | 300 | 730 | 1286 | $H_3PO_4$ | 2.10 | 8.8 | 13.2 | 71.75 | 93.95 |
| PA_6 | 300 | 750 | 1286 | $H_3PO_4$ | 2.10 | 8.8 | 13.2 | 86.61 | 93.23 |

The linear velocity of the liquid jet was about 100 m/s at the nozzle exit in the pilot-plant experiments mentioned in the table. This value was calculated from the diameter of the nozzle plate used and a throughput of 20 ml/h (25 g/h) of catalyst solution. The linear velocity of the vaporized acetic acid (1200 g/h, 600° C.) was about 4 m/s in the region of the catalyst spraying (tube diameter 20 mm).

In the experiments carried out, the catalyst, in each case as a solution in water and acetic acid, was admixed to the main stream as a continuous liquid jet. The acetic acid or water content admixed via the catalyst nozzle was in each case about 0.7 or 3.4 mol %, based on the preheated acetic acid main stream.

The catalyst content, based on the total amount of acetic acid used in the experiments (main stream and admixture in a catalyst reservoir) was in each case 1000 ppm.

Surprisingly, in the course of these measurements as given in the table, a long working life of the apparatus with the use of phosphoric acid was demonstrated and, in the context of the precision of measurement, the same selectivity and the same conversion rate based on the comparison experiment with TEP. A postulated rapid blockage of the tubular reactor by solid decomposition products of phosphoric acid (e.g. $P_2O_5$) was not observed, apparently due to the high temperature of the catalyst mixing construction and/or the good mixing and/or the dilution of the catalyst.

The advantages of the process according to the invention are essentially that triethylphosphate and other catalysts can, under optimized spraying conditions, be replaced by phosphoric acid with the same selectivity and conversion rate. This gives high potential savings in the industrial preparation of ketene and its secondary products.

What is claimed is:

1. A process for the catalytic pyrolysis of acetic acid for preparing ketene and/or derivatives thereof comprising the steps of spraying, as catalyst, phosphoric acid in the form of a continuous liquid jet into acetic acid vapor.

2. The process as claimed in claim 1, wherein the phosphoric acid is sprayed in pure or dilute form at elevated temperature into the acetic acid vapor.

3. The process as claimed in claim 1, wherein the phosphoric acid is added diluted with inorganic or organic solvents.

4. The process as claimed in claim 1, wherein the catalyst is diluted with water or acetic acid in a ratio of at most 1:100 and is sprayed at temperatures above 400° C. into acetic acid vapor.

5. The process as claimed in claim 1, wherein the catalyst includes the addition of gas.

6. The process as claimed in claim 1, wherein the phosphoric acid is sprayed at a pressure of 300 mbar.

7. The process as claimed in claim 3, wherein the inorganic or organic solvent is selected from the group consisting of water, methanol, ethanol and acetone.

8. The process as claimed in claim 5, wherein the gas is selected from the group consisting of nitrogen and ammonia.

* * * * *

UNITED STATES PATENT AND TRADEMARK OFFICE
CERTIFICATE OF CORRECTION

PATENT NO. : 6,395,935 B1
DATED : May 28, 2002
INVENTOR(S) : Jochem Baurmeister and Thomas Schäfer It is certified that error appears in the above-identified patent and that said Letters Patent is hereby corrected as shown below:

Column 4,
Line 28, delete "and/or derivatives thereof".
Line 29, after "acid" insert -- above 400ºC --.
Line 30, after "jet" insert -- at high impulse --.
Line 30, after "into" insert -- an --.
Line 30, delete "vapor" and insert -- mainstream, and wherein the catalyst is sprayed by ultrasonic nozzles or two-component nozzles and the velocity of the liquid jet is at least 10 times higher than that of the acetic acid mainstream --.
Lines 32-33, delete "at elevated temperature".
Line 33, delete "vapor" and insert -- mainstream --.
Line 39, delete "and is sprayed at temperatures above 400ºC into acetic acid vapor".

Signed and Sealed this

Twenty-ninth Day of July, 2003

JAMES E. ROGAN
*Director of the United States Patent and Trademark Office*